US00PP31754P2

(12) United States Plant Patent
Hansen

(10) Patent No.: US PP31,754 P2
(45) Date of Patent: May 12, 2020

(54) *ACHILLEA* PLANT NAMED 'SASSY SUMMER SILVER'

(50) Latin Name: ***Achillea* hybrid**
Varietal Denomination: Sassy Summer Silver

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,799

(22) Filed: Jan. 14, 2019

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14
See application file for complete search history.

*Primary Examiner* — Anne Marie Grunberg

(57) ABSTRACT

The new and distinct Yarrow, *Achillea* plant named 'Sassy Summer Silver', with narrow, silvery, fern-like foliage with moderately dissected lobules; tall, stiff, heavily branched peduncles with bright, golden yellow inflorescences, beginning in mid to late June and continuing for about six weeks. The new plant is useful for landscaping, as a specimen or en masse and as a cut flower.

1 Drawing Sheet

Botanical designation: *Achillea* hybrid.
Cultivar denomination: 'Sassy Summer Silver'.

STATEMENT REGARDING PRIOR DISCLOSURES UNDER 37 CFR 1.77(B)(6)

The first public disclosure of the claimed plant, in the form of a sale, was made by Walters Gardens, Inc. on Jul. 9, 2018. Prior to that, on Feb. 1, 2018 the claimed plant was displayed as a photograph with a brief description on a website operated by Walters Gardens, Inc., who obtained the plant and all information relating thereto, from the inventor. No plants of *Achillea* 'Sassy Summer Silver' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Sassy Summer Silver', by the cultivar name, 'Sassy Summer Silver', or as the new plant. The new plant was selected by the inventor as a single seedling resulting from an insect pollination cross in an isolation block between 'Moonshine' (not patented) crossed with an unknown male parent on Jun. 23, 2014 in research facility of a wholesale perennial grower based in Zeeland, Mich., USA. The seeds from this cross were collected late summer of 2014. The single seedling was then isolated and compared in subsequent years to other Yarrow and subsequently found to be different from all cultivars known to the discoverer and eventually given the breeder code 14-53-2.

Asexual propagation beginning in the August of 2015 at the same nursery in Zeeland, Mich., USA by basal tip cuttings has shown 'Sassy Summer Silver' to be stable and reproduce true to type in successive generations.

SUMMARY OF THE PLANT

*Achillea* 'Sassy Summer Silver' has not been observed in all possible environmental conditions. The phenotype may vary slightly with changes in environments such as light intensity, fertility, water availability, etc. without, however any variation in genotype.

*Achillea* 'Sassy Summer Silver' is distinct from all cultivars known to the inventor in the following traits:

1. Narrow, very silvery, fern-like foliage with medium height and dense upright habit.
2. Numerous large panicles of bright, golden yellow inflorescences.
3. Ray florets and disk florets the same bright, golden yellow coloration.
4. Heavily-branched peduncles with center main cluster to about 11 cm across.
5. Sturdy stems withstand wind and rain.
6. Flowering begins mid to late June and continues for six weeks.

Plants of *Achillea* 'Sassy Summer Silver' are most similar to 'Moonshine' (not patented) 'Coronation Gold' (not patented), 'Sunny Seduction' U.S. Plant Pat. No. 20,808, 'Anblo' U.S. Plant Pat. No. 8,828, 'Sassy Summer Lemon' U.S. Plant patent application Ser. No. 16/350,800 and 'Parker's Variety' (not patented). 'Moonshine' has deeper gold floret coloration and the foliage shows susceptibility to *botrytis*. 'Coronation Gold' has deeper yellow floret color and is significantly taller in habit. 'Sunny Seduction' has slightly deeper yellow floret color and is slightly taller in habit in side by side trials. 'Anblo', sold under the tradename ANTHEA™ has paler yellow florets and is slightly shorter than the new plant. 'Sassy Summer Lemon' has a lighter yellow floret color, flowers at least a week earlier, and is taller in habit with fewer whitish hairs on the foliage and deeper cleft lobules. 'Parker's Variety' is much taller and less compact in habit and the florets are deeper gold colored.

BRIEF DESCRIPTION OF THE DRAWINGS

The color drawings illustrate the overall characteristics of *Achillea* 'Sassy Summer Silver' as a three-year-old plant grown in a full-sun trial garden in Zeeland, Mich. The colors are as true as reasonably possible given the technology available. The color values may vary slightly depending on light intensity and quality.

DETAILED BOTANICAL DESCRIPTION

Figure 1:
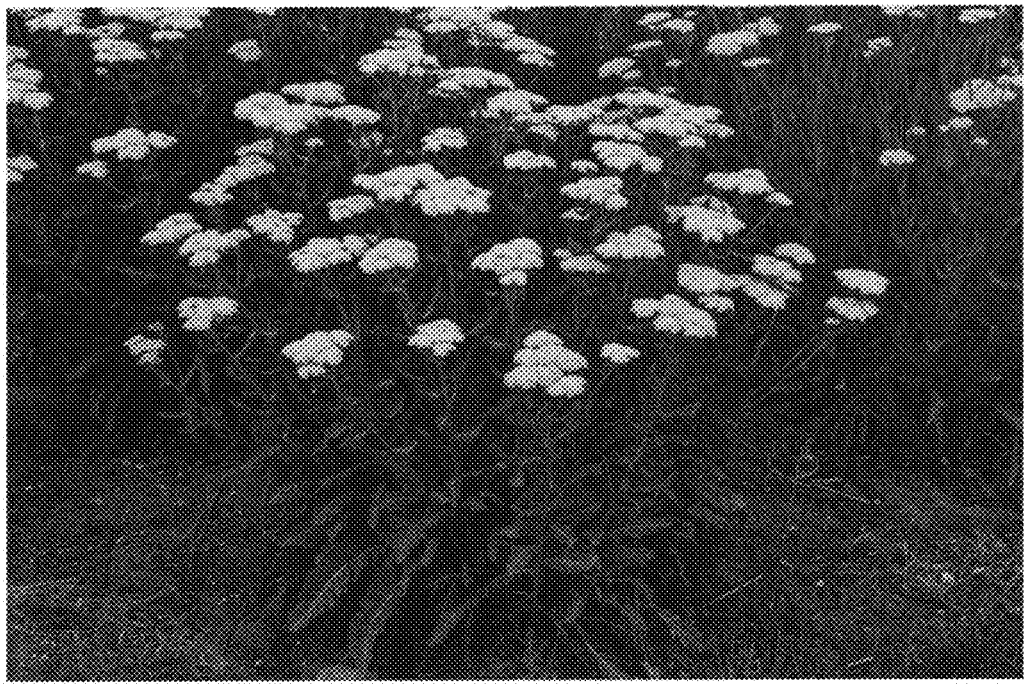
FIG. 1 shows the new plant in a trial facility.
Figure 2:
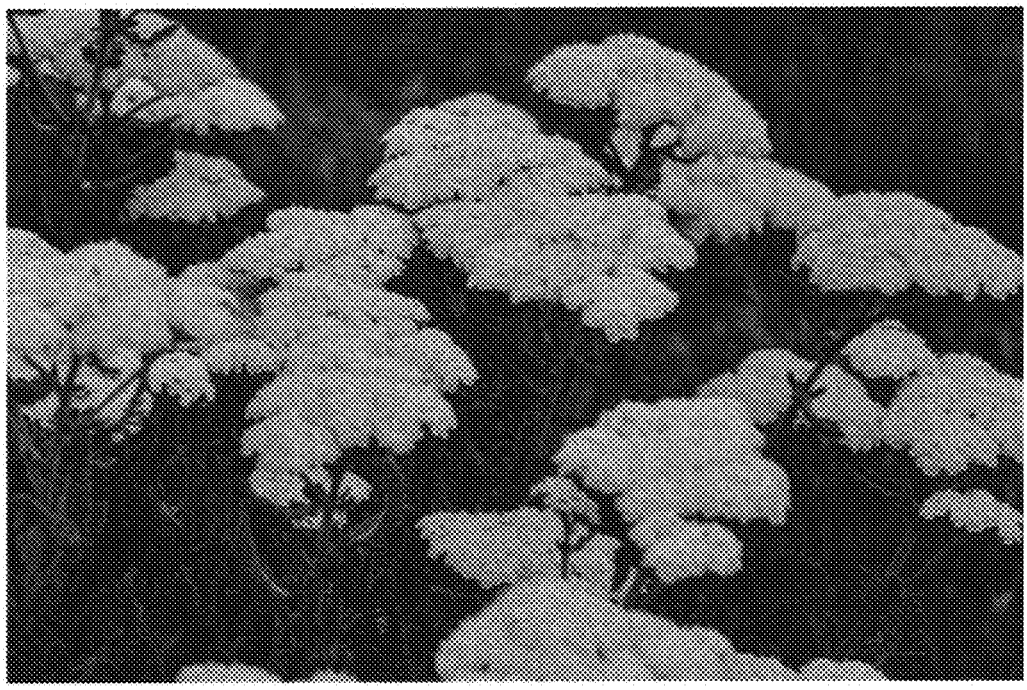
FIG. 2 shows a close-up of the flowers and buds of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent is *Achillea* 'Moonshine'; the male or pollen parent unknown;

Asexual propagation: Basal shoot cuttings, about 10 to 14 days to initiate roots; time to finish as # 1 field grown size about 4 months from a 25 mm liner;

Plant habit: Dense axillary branches; upright, heavily-branched, herbaceous, winter-hardy, perennial mound; up to 56.0 cm tall and 67.0 cm wide; average about 52.0 cm tall and about 58.0 cm across;

Stems: Cylindrical; lanulose; branching near top; about 6.0 mm diameter at base and 50.0 cm long; up to 25 stems per plant, average 20 stems per plant;

Stem color: Nearest blend between RHS N138D and RHS 138A;

Internodes: About 17 per stem; same color as surrounding stem; average internode spacing about 2.9 cm;

Leaves: Alternate; glabrous; pinnatisect with lobules moderately dissected; lanceolate; acute apex; base attenuate; sessile except proximal leaves; lanulose abaxial and adaxial; up to 21.0 cm long and 5.0 cm wide with individual lobes to 10.0 mm wide and 2.0 cm long, average about 19.0 cm long and 4.5 cm wide; fragrance herbal;

Leaf color: Young expanding and mature leaves adaxial nearest blend between RHS 132B and RHS N138B and young expanding and mature abaxial between RHS 132B and RHS N138C;

Veins: Pinnate; only abaxial midrib obvious;

Midrib color: Adaxial and abaxial between RHS 132C and RHS 132D;

Petiole: To 5.0 cm long and 4.0 mm wide at base;

Inflorescence: Radiate; capitate; composite consisting of about five ray and about twelve disk florets; on heavily branched terminal stems; individual inflorescence about 8.0 mm diameter, about 6.0 mm tall from bottom of involucral bracts to top of exserted anthers; disk about 4.0 mm across; attitude mostly upright; producing branched stems with about 200 inflorescences per stem about 12.0 cm across;

Receptacle: About 4.0 mm tall and 5.0 mm diameter; color nearest RHS 148C;

Inflorescence fragrance: Not detected;

Phyllaries: About ten in two whorls; lanceolate; acute apex; truncate base; margin entire; outer or lower set about 2.0 mm long and 1.0 mm across, inner set about 3.0 mm long and 1.0 mm across; glabrous adaxial, pubescent abaxial; tightly adpressed against ray petals;

Phyllary color: Nearest RHS 147C adaxial and abaxial, with margins nearest RHS 193C;

Flowering period: Mid to late June, for about 6 weeks;

Flower longevity: 4 to 6 days;

Inflorescence buds: Ovoid; with ray florets still partially enclosed in phyllaries about 4.0 mm tall and 2.5 mm across;

Inflorescence bud color: Exposed ray florets nearest RHS 15D just above phyllaries; phyllaries color nearest RHS 146C;

Peduncle: Cylindrical; lanulose; strong; upright attitude; heavily branched; up to 6.0 mm diameter at base, average 5.0 mm diameter; and 50.0 cm long, flowering in upper 14.0 cm to about 12.0 cm across; branches to about 10.0 cm long and 4.0 mm diameter at base;

Peduncle color: Nearest RHS 191B;

Ray florets: Imperfect; staminate; typically about five per inflorescence; containing only gynoecium with style about 2.5 mm long and split stigma;

Ray floret ligule: Blade with basal claw; blade apex tri-lobed, margin entire; base claw, attenuate; opening to form 90° angle; glabrous adaxial and adaxial; about 4.0 mm long and about 5.0 mm wide; basal claw about 1.5 mm long and about 0.5 mm across;

*Ray floret ligule color*.—Adaxial between RHS 16B and RHS 20B, abaxial nearest RHS 11C and claw base nearest RHS NN155C with little to no change in color with maturity.

*Style*.—Cylindrical; about 2.0 mm long and 0.2 mm diameter; exserted; color nearest RHS 18B.

*Stigma*.—Bifid; about 1.5 mm long and 0.2 mm diameter; color nearest RHS 18B.

Disk florets: About twelve per capitulum; tubular; glabrous; consisting of tepals, staminal tube and pistil; size about 3.5 mm long by 1.0 mm wide at apex;

*Tepals*.—Five; 2.5 mm long and 0.7 mm wide, fused in the basal 2.0 mm, acute apex.

*Tepal color*.—Between RHS 16B and RHS 20B.

*Staminal tube*.—Made up of five adnate stamens; about 2.0 mm long.

*Filaments*.—Cylindrical; about 0.7 mm long and 0.1 mm diameter; color nearest RHS NN155A.

*Anther*.—About 1.0 mm long and 0.5 mm across; color nearest RHS 22A.

*Pollen*.—Fine, round, closest to RHS 22A.

*Style*.—Cylindrical; exserted; about 2.0 mm long and 0.2 mm diameter; color nearest RHS 18B.

*Stigma*.—Bifid; reflexing as it matures; about 1.5 mm long; color nearest RHS 18B.

Seed: Flattened deltoid; acute apex and truncate base; surface glabrous; about 2.0 mm long and 0.7 mm across base;

Seed color: Between RHS 165A and RHS 165B in center and RHS 161D around edges;

*Achillea* 'Sassy Summer Silver' does best in well-drained soils and is tolerant of winter temperatures as low as −35° C. and summer temperatures as high as 38° C. 'Sassy Summer Silver' resists lodging from heavy winds and rains, but has not shown any tolerance or resistance to diseases common among Yarrow include *botrytis* (*Botrytis cinerea*) and stem rot (*Pythium* and *Phytophthora*) or to insect pests.

I claim:

1. The new and distinct cultivar of *Achillea* plant named 'Sassy Summer Silver' as described and illustrated.

* * * * *